(12) United States Patent
Dunham et al.

(10) Patent No.: US 7,409,043 B2
(45) Date of Patent: Aug. 5, 2008

(54) METHOD AND APPARATUS TO CONTROL RADIATION TUBE FOCAL SPOT SIZE

(75) Inventors: Bruce Matthew Dunham, Mequon, WI (US); Jonathan Richard Schmidt, Wales, WI (US); Sergio Lemaitre, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 65 days.

(21) Appl. No.: 11/439,027

(22) Filed: May 23, 2006

(65) Prior Publication Data

US 2007/0274457 A1    Nov. 29, 2007

(51) Int. Cl.
H05G 1/32 (2006.01)
H05G 1/34 (2006.01)
H05G 1/46 (2006.01)

(52) U.S. Cl. .............. 378/115; 378/110; 378/112; 378/113

(58) Field of Classification Search ........... 378/110, 378/112, 113, 115
See application file for complete search history.

(56) References Cited

U.S. PATENT DOCUMENTS

| | | | | |
|---|---|---|---|---|
| 2,340,363 A * | 2/1944 | Atlee et al. | .............. | 378/113 |
| 2,878,393 A * | 3/1959 | Graves | .............. | 250/399 |
| 3,103,591 A * | 9/1963 | Rogers et al. | .............. | 378/106 |
| 3,882,339 A * | 5/1975 | Rate et al. | .............. | 378/124 |
| 3,986,064 A * | 10/1976 | Oosterkamp et al. | .............. | 378/125 |
| 5,020,086 A * | 5/1991 | Peugeot | .............. | 378/113 |
| 5,023,895 A * | 6/1991 | McCroskey et al. | .............. | 378/4 |
| RE33,634 E * | 7/1991 | Yanaki | .............. | 378/110 |
| 5,550,889 A * | 8/1996 | Gard et al. | .............. | 378/113 |
| 5,907,595 A * | 5/1999 | Sommerer | .............. | 378/136 |
| 6,104,781 A * | 8/2000 | Buchmann | .............. | 378/101 |
| 6,310,938 B1 | 10/2001 | Toth et al. | | |
| 6,327,331 B1 * | 12/2001 | Toth et al. | .............. | 378/20 |
| 6,411,677 B1 | 6/2002 | Toth et al. | | |
| 6,652,143 B2 * | 11/2003 | Popescu | .............. | 378/207 |
| 6,785,359 B2 * | 8/2004 | Lemaitre | .............. | 378/136 |
| 6,819,739 B2 * | 11/2004 | Eppler | .............. | 378/21 |
| 6,950,492 B2 * | 9/2005 | Besson | .............. | 378/5 |
| 6,980,623 B2 | 12/2005 | Dunham et al. | | |
| 2002/0021785 A1 | 2/2002 | Toth et al. | | |
| 2005/0069086 A1 * | 3/2005 | Deych et al. | .............. | 378/112 |
| 2005/0169428 A1 * | 8/2005 | Hardesty | .............. | 378/110 |

* cited by examiner

*Primary Examiner*—Edward J. Glick
*Assistant Examiner*—Thomas R Artman
(74) *Attorney, Agent, or Firm*—Dean D. Small; Small Patent Law Group

(57) ABSTRACT

A method for controlling focal spot size changes of an x-ray source in an imaging system includes measuring focal spot sizes as a function of a plurality of x-ray source operating parameters, determining a calibration table or transfer function utilizing the measured focal spot sizes as a function of the plurality of x-ray tube operating parameters, and utilizing the calibration table or transfer function to control focal spot size variations during operation of the imaging system.

23 Claims, 3 Drawing Sheets

METHOD AND APPARATUS TO CONTROL RADIATION TUBE FOCAL SPOT SIZE

BACKGROUND OF THE INVENTION

This invention relates generally to radiation imaging devices, and more particularly to methods and apparatus for controlling a focal spot of an x-ray tube of an imaging apparatus.

In some known CT imaging system configurations, an x-ray source, such as an x-ray tube, projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

The focal spot size of x-ray tubes used in CT imaging systems can vary substantially as the mA and kV values change over a wide range. X-ray tubes are generally required to produce currents varying from a few mA up to maximum currents near 1 Amp. Due to space charge forces on the electron beam, focal spot size can vary substantial over the entire mA range, as well as the kV range. As a result, artifacts can occur in images produced by a CT imaging system utilizing such tubes. For known prior art CT imaging systems, there is no way to control this variation other than use an an x-ray tube designed to keep the focal spot size within a given range. If the designed range is too wide, image quality, tube performance, or both may be degraded. In particular, as CT imaging systems are being built with increasingly wide detectors and thin slices, variations in spot size with mA is causing increasingly noticeable artifacts in outer rows of volume computed tomographic (VCT) images.

X-ray tubes having dynamic focal spot control have recently become available. These x-ray tubes use sets of control plates near the filament of the tube to shape and deflect the electron beam or a dynamic magnetic field, and thus the x-ray beam. These tubes now make it possible to dial in a given focal spot size by sending appropriate control (bias) voltages to the cathode of the tube or magnetic field controls signals to an magnet.

BRIEF DESCRIPTION OF THE INVENTION

Therefore, in one aspect, the present invention provides a method for controlling focal spot size changes of an x-ray source in an imaging system. The method includes measuring focal spot sizes as a function of a plurality of x-ray source operating parameters, determining a calibration table or transfer function utilizing the measured focal spot sizes as a function of the plurality of x-ray tube operating parameters, and utilizing the calibration table or transfer function to control focal spot size variations during operation of the imaging system.

In another aspect, the present invention provides an imaging system having an x-ray source, an x-ray source controller configured to control the x-ray source, and a detector array responsive to x-ray radiation emitted by the x-ray source. The imaging system is configured to measure focal spot sizes on the detector array as a function of a plurality of operating parameters of the x-ray source, determine a calibration table or transfer function utilizing the measured focal spot sizes as a function of the plurality of x-ray source operating parameters, and utilize the calibration table or transfer function to control focal spot size variations on the detector array during operation of the imaging system.

It will be observed that some configurations of the present invention allow a focal spot to be maintained at a given size over a wide range of mA and kV values. Also, some configurations permit the size and shape to be optimized to allow the x-ray tube to operate at the highest peak power possible, without having to limit the power to account for variations in the spot size.

Similar plots can be made for a magnetic field value for sources using one or more magnets.

Figure 4:
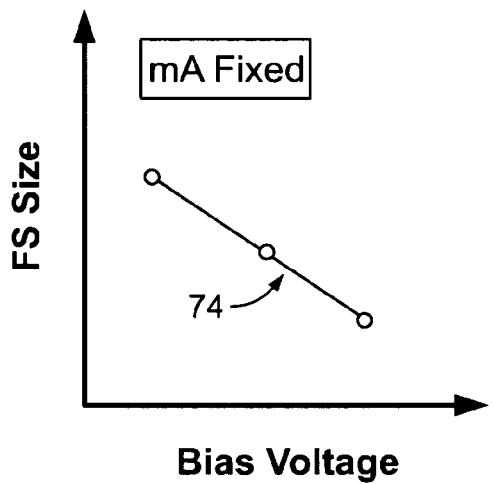

FIG. 4 is a plot of focal spot size as a function of x-ray tube bias voltage, at a particular, fixed mA. A plurality of such plots are determined at different, fixed mAs via a calibration procedure of the CT imaging system of FIG. 1.

Figure 3:
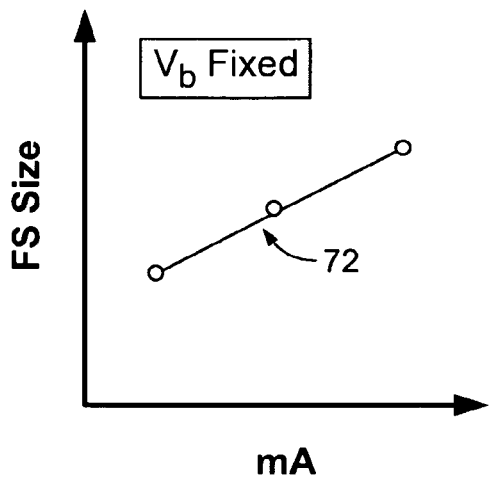
FIG. 3 is a plot of focal spot size as a function of x-ray source mA, at a particular, fixed bias voltage. A plurality of such plots are determined at different, fixed bias voltages via a calibration procedure of the CT imaging system of FIG. 1.
Figure 5:
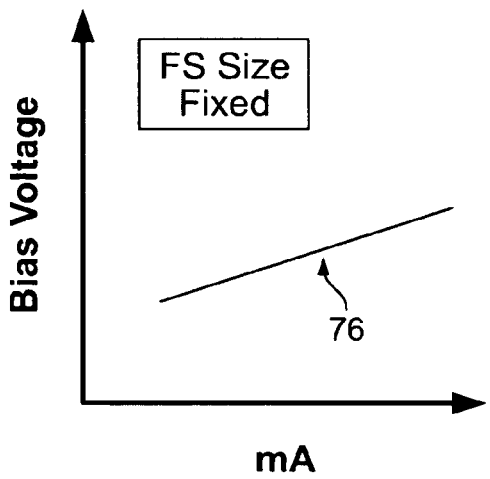

FIG. 5 is a plot representing a calibration table or function that can be determined from the plots of FIGS. 3 and 4. The plot of FIG. 5 shows the various combinations of mA and bias voltage that can be used to keep the focal spot size of the CT imaging system of FIG. 1 at a particular, fixed size. A plurality of plots similar to FIG. 5 can be determined for different focal spot sizes.

Figure 1:
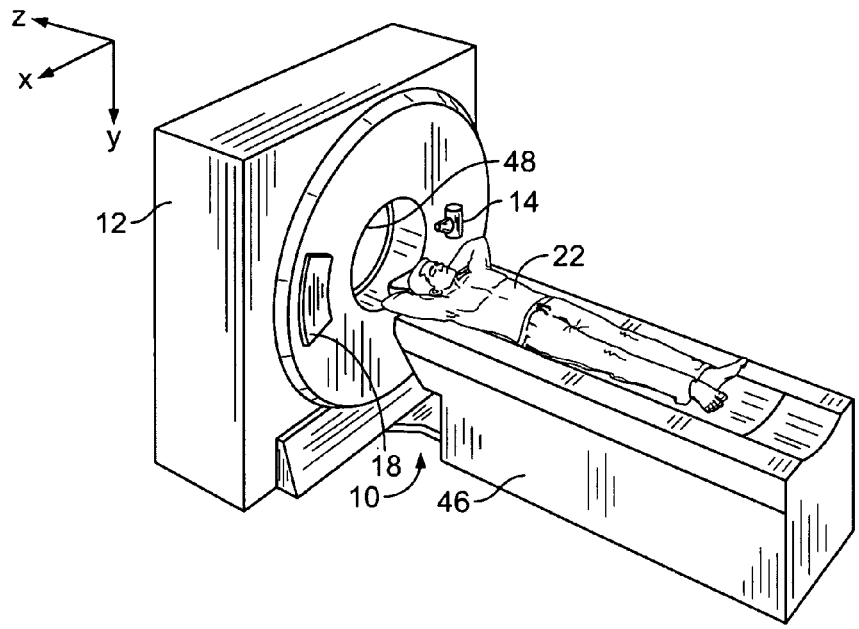
FIG. 1 is a pictorial drawing of a computed tomographic (CT) imaging system.
Figure 6:
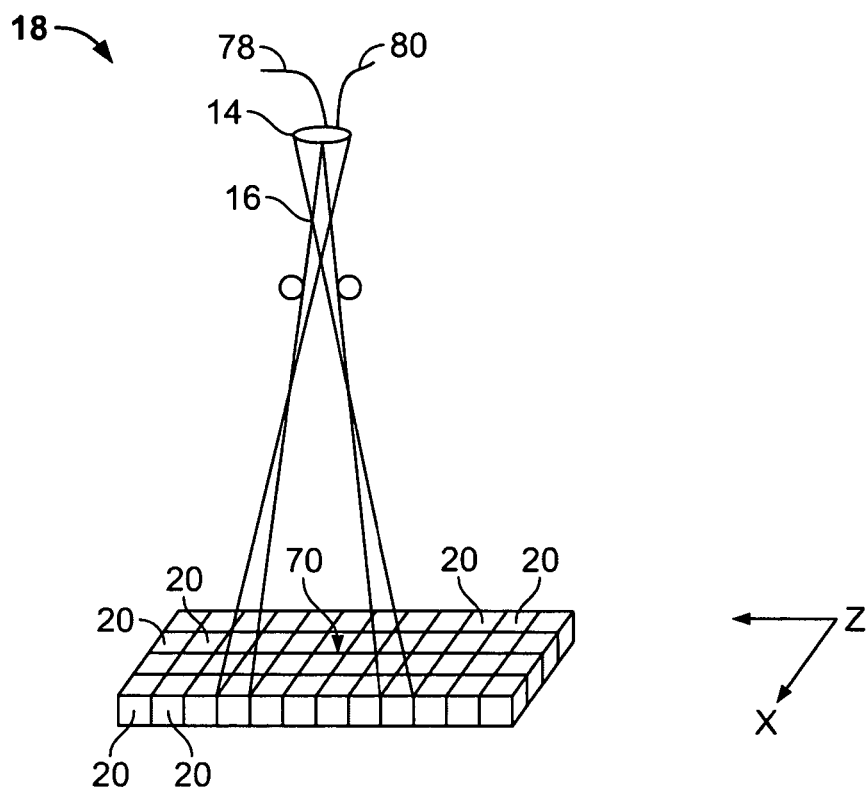

FIG. 6 is a representation of a portion of the CT imaging system of FIG. 1 showing a focal spot of the x-ray tube of the imaging system on the detector array.

Figure 7:
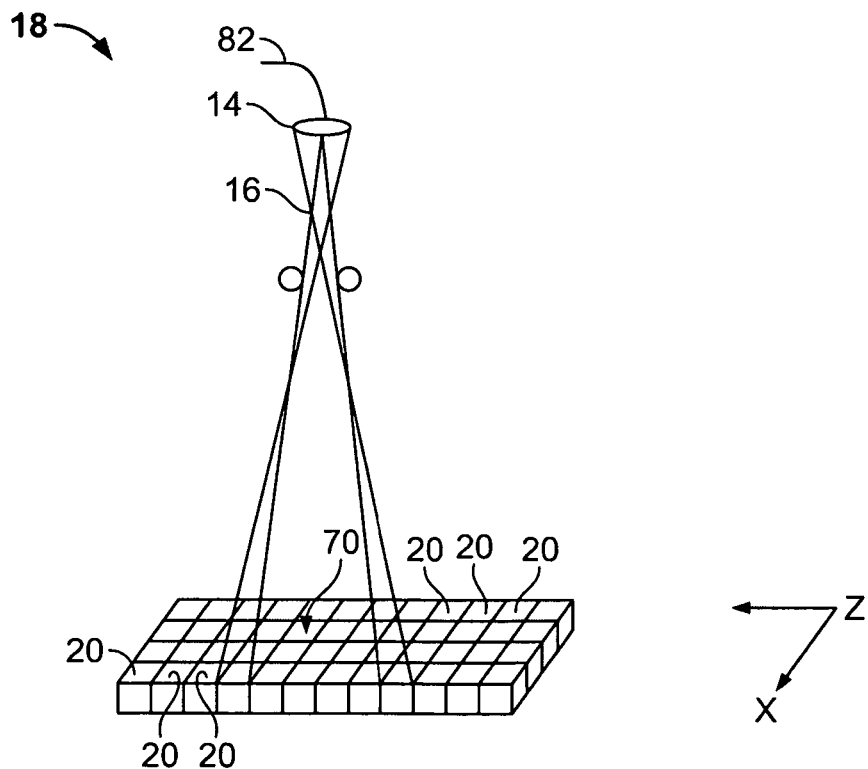

FIG. 7 is a representation of a portion of a CT imaging system similar to that shown in FIG. 6, but wherein the x-ray tube includes a magnetic quadrupole field adjustment.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
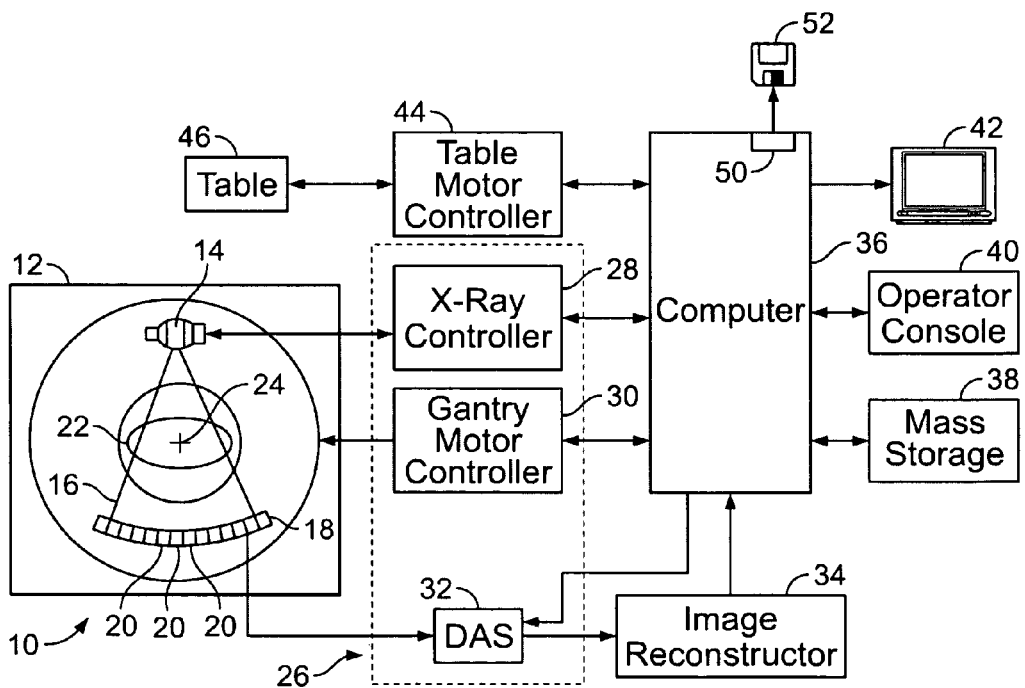
FIG. 2 is a schematic block diagram of the CT imaging system of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. X-ray tube 14 in various configurations of the present invention has a dynamic focal spot control, thereby making it possible to compensate for changes in spot size by adjusting the voltages on field control plates. In some configurations of the present invention, this compensation is provided by performing a system level calibration in which the focal spot size (length and width) is measured as a function of mA, kV, and bias voltage on the plates of the x-ray tube [or magnetic field on magnet(s)]. Then a calibration table or transfer function is determined from which the bias voltage that the tube must operate at to keep the focal spot size at a selected value for any scan condition.

Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can comprise specialized hardware and/or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT, such as other types of x-ray imaging systems, mammography systems, radiation therapy systems. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center and various types of x-ray inspection systems.

In some configurations of the present invention, CT imaging system 10 utilizes an x-ray source 14 that has sets of electric field control plates near its filament to shape and deflect the electron beam, and thus x-ray beam 16. A selected focal spot size is maintained by determining and sending appropriate control voltages to the cathode of tube 14.

For example, in some configurations of the present invention, changes in spot size are compensated by adjusting voltages on field control plates of tube 14. In some configurations, a system level calibration is performed in which focal spot size (length and width) is measured as a function of mA, kV, and bias voltage on the plates of tube 14. A calibration table or transfer function is then determined. This table is used to determined the correct bias voltage to apply to tube 14 to keep the focal spot size at a given value for any scan condition.

For example, some configurations of the present invention perform a real-time measurement of the focal spot size. The measurement is used as a feedback signal to x-ray tube 14 to adjust the focal spot to a desired size. In some CT imaging system configurations 10, the measurement of focal spot size is performed only in a z-direction because in this direction collimator blades produce a shadow on the detector, whereas in the x direction, no hard edges exist. However, a hard edge that casts a shadow on an edge of the detector out of the imaging field of view is added in some configurations to allow focal spot size to be determined in the x-direction.

Advantageous, various configurations of the present invention can maintain focal spot of a selected size over a wide range of mA and kV values. Thus, the size and shape of the focal spot can be controlled to allow x-ray tube 14 to operate at a high peak power, or even the highest peak power possible, without having to limit power to account for variations in the spot size. In addition, when using dose reduction features that are present in some configurations of imaging system 10, the mA may vary between the minimum to maximum mA values for x-ray tube 14 within a single scan. Without a way to control the spot size, image resolution could be degraded. However, by using a calibration table or by providing feedback, the bias voltage is adjusted during the scan in various configurations of the present invention, thereby maintaining spot size.

In some configurations of the present invention and referring to FIGS. 3, 4, and 5, curves 72 and 74 of FIGS. 3 and 4 are either measured or simulated, wherein curve 72 of FIG. 3 is focal spot size versus mA for a given bias voltage, and curve 74 of FIG. 4 is focal spot size versus bias voltage for a given mA. Curve 76 of FIG. 5 is a transfer function determined mathematically using curves 72 and 74 of FIGS. 3 and 4 to find a bias voltage needed to keep the focal spot size constant as a function of mA. (A calibration table may be determined instead of a transfer function.)

Although curves can be linear, as shown in FIGS. 3, 4, and 5, the curves need not be linear as shown. Non-linear curves can be helpful in configurations in which there are significant second-order or higher cross-terms between mA, V, and size, for example.

Thus, referring to FIG. 6, some configurations of the present invention provide a method for controlling focal spot 70 size changes of an x-ray tube 14 in a CT imaging system 10. The method includes measuring focal spot 70 sizes as a function (e.g., curves 72 and 74 of FIGS. 3 and 4) of a plurality of x-ray tube 14 operating parameters, determining a calibration table or transfer function (e.g., a function such as that represented by curve 76 of FIG. 5) utilizing the measured focal spot 70 sizes as a function of the plurality of x-ray tube 14 operating parameters, and utilizing the calibration table or transfer function 76 to control focal spot 70 size variations during operation of CT imaging system 10. In some configurations and referring to FIG. 6, the plurality of x-ray tube operating parameters include mA, kV, and bias voltage on plates 78, 80 of x-ray tube 14.

Also in some configurations, utilizing the calibration table or transfer function 76 to control focal spot 70 size variations during operation of CT imaging system 10 further comprises utilizing calibration table or transfer function 76 to control focal spot 70 size changes as mA, kV or both vary during operation of CT imaging system 10.

In some configurations, the measuring of focal spot 70 sizes is performed only in a z-direction of CT imaging system 10. However, in some configurations, the measuring of focal spot 70 sizes is performed in both a z-direction of the CT imaging system 10 and an x-direction of the CT imaging system 10.

In some configurations, utilizing the calibration table or transfer function 76 to control focal spot 70 size changes as mA, kV or both vary during operation of CT imaging system further comprises controlling a bias voltage of x-ray tube 14. However, in some configurations and referring to FIG. 7, x-ray tube 14 includes a magnetic quadrupole field adjustment 82, and the magnetic quadrupole field in x-ray tube 14 is adjusted.

Referring to FIGS. 1 and 2, some configurations of the present invention comprise a CT imaging system 10 having an x-ray tube 14, an x-ray tube controller 28 configured to control x-ray tube 14, a detector array 18 responsive to x-ray radiation 16 emitted by x-ray tube 14. Referring to FIGS. 3 through 6, CT imaging system 10 is configured to measure focal spot 70 sizes on detector array 18 as a function (e.g., curves 72 and 74) of a plurality of operating parameters of x-ray tube 14, determine a calibration table or transfer function 76 utilizing the measured focal spot 70 sizes as a function of the plurality of x-ray tube operating parameters, and utilize the calibration table or transfer function 76 to control focal spot 70 size variations on detector array 18 during operation of CT imaging system 10. For example, image reconstructor 34 and/or computer 36 are used in some configurations to measure the focal spot sizes on the detector array, to determine the calibration table or transfer function, and, in conjunction with x-ray controller 28, control focal spot size variations on the detector array during operation of imaging system 10 by controlling, for example, bias voltages on x-ray tube 14.

In some configurations of CT imaging system 10, the plurality of x-ray tube 14 operating parameters include mA, kV, and bias voltage on plates of x-ray tube 14. Also in some configurations, utilizing the calibration table or transfer function to control focal spot size variations comprises utilizing the calibration table or transfer function to control focal spot size changes as mA, kV or both vary during operation of the CT imaging system.

In some configurations, CT imaging system 10 is configured to measure focal spot sizes only in a z-direction of imaging system 10. In other configurations, CT imaging system 10 is configured to measure focal spot sizes in both a z-direction and an x-direction. CT imaging system 10 is configured in some configurations to control focal spot size changes as mA, kV or both vary during operation of the CT imaging system further by controlling the bias voltage of the x-ray tube. Also in some configurations, controlling focal spot size changes further comprises adjusting a magnetic quadrupole field in the x-ray tube.

It will thus be appreciated that various configurations of the present invention allow a focal spot to be maintained at a given size over a wide range of mA and kV values. Also, the size and shape of the focal spot can be optimized in some configurations to allow the x-ray tube to operate at the highest peak power possible, without having to limit the power to account for variations in the spot size.

While the invention has been described in terms of various specific embodiments, those skilled in the art will recognize that the invention can be practiced with modification within the spirit and scope of the claims.

What is claimed is:

1. A method for controlling focal spot size changes of an x-ray source in an imaging system, said method comprising:
   measuring focal spot sizes as a function of a plurality of x-ray source operating parameters;
   determining calibration information utilizing the measured focal spot sizes as a function of the plurality of x-ray tube operating parameters;
   selecting a focal spot size for a predetermined scan condition; and
   utilizing the calibration information to maintain the focal spot size selected during operation of the imaging system.

2. A method in accordance with claim 1 wherein the imaging system is a CT imaging system.

3. A method in accordance with claim 1 wherein the plurality of x-ray source operating parameters include mA, kV, and bias voltage on plates of the x-ray source or current in an electromagnet or electromagnets influencing the x-ray source.

4. A method in accordance with claim 1 wherein the plurality of x-ray source operating parameters include at least mA and kV, and further wherein said utilizing the calibration table or transfer function to control focal spot size variations during operation of the imaging system further comprises utilizing the calibration table or transfer function to control focal spot size changes as mA, kV or both vary during operation of the imaging system.

5. A method in accordance with claim 1 wherein said determining calibration information comprises determining a calibration table.

6. A method in accordance with claim 1 wherein said determining calibration information comprises determining a transfer function.

7. A method in accordance with claim 1 wherein the imaging system is a CT imaging system, and said measuring focal spot sizes is performed only in a z-direction of the imaging system.

8. A method in accordance with claim 1 wherein the imaging system is a CT imaging system, and said measuring focal spot sizes is performed in both a z-direction of the imaging system and an x-direction of the imaging system.

9. A method in accordance with claim 1 wherein said utilizing the calibration information to control focal spot size changes further comprises controlling a bias voltage of the x-ray source as mA, kV or both vary during operation of the imaging system or adjusting a magnetic field influencing the x-ray source as mA, kV or both vary during operation of the imaging system.

10. A method in accordance with claim 1 further comprising utilizing the focal spot size measurement to adjust the size of the focal spot to the selected focal spot size.

11. A method in accordance with claim 1 further comprising utilizing a feedback signal to adjust the focal spot size during a scanning operation.

12. A method in accordance with claim 1 wherein selecting a focal spot size for a predetermined scan condition comprises selecting a focal spot size to be used during at least one of an axial scan and a helical scan.

13. A method in accordance with claim 1 further comprising utilizing a feedback signal to adjust the focal spot size in the z-direction when performing a helical scanning operation.

14. An imaging system having an x-ray source, an x-ray source controller configured to control said x-ray source, a detector array responsive to x-ray radiation emitted by said x-ray source, and said imaging system configured to:
   measure focal spot sizes on the detector array as a function of a plurality of operating parameters of said x-ray source;
   determine calibration information utilizing the measured focal spot sizes as a function of the plurality of x-ray source operating parameters;
   select a focal spot size for a predetermined scan condition; and
   utilize the calibration information to maintain the focal spot size selected on the detector array during operation of the imaging system.

15. An imaging system in accordance with claim 14 wherein the imaging system is a CT imaging system.

16. An imaging system in accordance with claim 14 wherein the plurality of x-ray source operating parameters include mA, kV, and bias voltage on plates of said x-ray source.

17. An imaging system in accordance with claim 14 wherein the plurality of x-ray source operating parameters include mA, kV, and current in an electromagnet or electromagnets influencing said x-ray source.

18. An imaging system in accordance with claim 14 wherein the plurality of x-ray source operating parameters include at least mA and kV, and wherein to utilize the calibration table or transfer function to control focal spot size variations during operation of the imaging system, said imaging system configured to utilize the calibration information to control focal spot size changes as mA, kV or both vary during operation of the imaging system.

19. An imaging system in accordance with claim 14 wherein to determine calibration information, said imaging system configured to determine a calibration table.

20. An imaging system in accordance with claim 14 wherein to determine calibration information, said imaging system configured to determine a transfer function.

21. An imaging system in accordance with claim 14 wherein said imaging system is a CT imaging system configured to measure focal spot sizes only in a z-direction of the imaging system.

22. An imaging system in accordance with claim 14 wherein said imaging system is a CT imaging system configured to measure focal spot sizes in both a z-direction of the imaging system and an x-direction of the imaging system.

23. An imaging system in accordance with claim 14 wherein to utilize the calibration table or transfer function to control focal spot size changes, said imaging system configured to control a bias voltage of the x-ray source as mA, kV or both vary during operation of the imaging system or to adjust a magnetic field in the x-ray source as mA, kV or both vary during operation of the imaging system.

* * * * *